United States Patent
Driks

(10) Patent No.: US 10,375,955 B2
(45) Date of Patent: Aug. 13, 2019

(54) METHODS, FORMULATIONS, AND KITS FOR BACTERIAL DEGRADATION

(71) Applicant: Loyola University of Chicago, Maywood, IL (US)

(72) Inventor: Adam Driks, Maywood, IL (US)

(73) Assignee: Loyola University Chicago, Maywood, IL (US)

( * ) Notice: Subject to any disclaimer, the term of this patent is extended or adjusted under 35 U.S.C. 154(b) by 0 days.

(21) Appl. No.: 15/707,372

(22) Filed: Sep. 18, 2017

(65) Prior Publication Data

US 2018/0027808 A1 Feb. 1, 2018

Related U.S. Application Data

(62) Division of application No. 14/327,005, filed on Jul. 9, 2014, now abandoned.

(60) Provisional application No. 61/843,952, filed on Jul. 9, 2013.

(51) Int. Cl.

| *A01N 63/02* | (2006.01) |
| *A01N 31/02* | (2006.01) |
| *C12N 9/00* | (2006.01) |
| *A01N 65/08* | (2009.01) |
| *C12N 9/94* | (2006.01) |

(52) U.S. Cl.
CPC ............ *A01N 31/02* (2013.01); *A01N 63/02* (2013.01); *A01N 65/08* (2013.01); *C12N 9/00* (2013.01); *C12N 9/94* (2013.01)

(58) Field of Classification Search
None
See application file for complete search history.

(56) References Cited

U.S. PATENT DOCUMENTS

| 4,670,178 A | * | 6/1987 | Huth | A61L 12/124 422/28 |
| 2009/0311395 A1 | * | 12/2009 | Cervin | A61K 31/327 426/332 |

OTHER PUBLICATIONS

Indest et al., Journal of Food Science, 2009, vol. 74: R73-R78.*
Suzuki et al., Journal of Bacteriology, 1969, 98:238-245.*
Dubberke et al., Am. J. Infect. Control. 2007, 35: 315-318.*

* cited by examiner

*Primary Examiner* — Allison M Fox
*Assistant Examiner* — Qing Xu
(74) *Attorney, Agent, or Firm* — Hartman Global IP Law; Gary M. Hartman; Domenica N. S. Hartman

(57) ABSTRACT

Methodologies, formulations, and kits suitable for decontaminating environments containing bacterial spores by degrading the spores. Formulations contain papain and at least one germinant. Methods for killing bacterial spores include contacting the spores with the formulation for a duration sufficient to initiate germination of the bacterial spores. The spores are then killed with the papain in the formulation, or are rendered by the papain susceptible to being killed by a reagent.

17 Claims, 4 Drawing Sheets

METHODS, FORMULATIONS, AND KITS FOR BACTERIAL DEGRADATION

CROSS REFERENCE TO RELATED APPLICATIONS

This is a division patent application of co-pending U.S. patent application Ser. No. 14/327,005, filed Jul. 9, 2014, which claims the benefit of U.S. Provisional Application No. 61/843,952, filed Jul. 9, 2013, the contents of which are incorporated herein by reference.

STATEMENT REGARDING FEDERALLY SPONSORED RESEARCH

This invention was made with government support under Contract No. HDTRA1-11-1-0051 awarded by the Defense Threat Reduction Agency (DTRA). The Government has certain rights in the invention.

BACKGROUND OF THE INVENTION

The present invention generally relates to the field of bacteriology. More particularly, this invention relates to methods and formulations for degrading bacterial spores (e.g., neutralizing, destroying, or killing bacterial spores), wherein the formulations contain low-toxicity, human-compatible, and materials-compatible reagents and are conducive to safe and facile containment, delivery, and application by a human.

Anthrax is an acute disease caused by exposure to the bacterium *Bacillus anthracis*. Most forms of the disease are lethal, affecting both humans and animals. Like many other members of the genus *Bacillus, Bacillus anthracis* can form dormant endospores which are often referred to as "spores." These dormant spores are able to survive in harsh conditions for decades or even centuries. When these dormant spores are inhaled, ingested, or come into contact with a skin lesion on a host, they may become reactivated and rapidly multiply.

Due to their lethal effects and rugged tenacity in a wide range of environments, *Bacillus anthracis* spores (anthrax spores) can be utilized as an effective biological weapon. Correspondingly, technologies to destroy or decontaminate *Bacillus anthracis* culture facilities are a major national security need. Generally, large quantities of bleach or other toxic chemical reagents are required to degrade *Bacillus anthracis* spores and cultures for the production of spores. A primary approach to the decontamination of a *Bacillus anthracis* culture facility is the application of a spore-degrading chemical reagent into the facility. For this approach to be practical, the chemical reagent must be sufficiently easy to transport and handle (e.g., low human toxicity and easily contained) so that it may be safely delivered in potentially challenging operational environments. Harsh, reactive chemical reagents that may endanger operators and require special equipment are undesirable, as are chemical reagents that may degrade equipment or other inert materials within the operational environment, referred to herein as reagents that do not have high materials-compatibility.

*Clostridium difficile* spores are the primary causative agent of the major hospital-associated disease *Clostridium difficile* infection (CDI). Therefore, control of CDI in the hospital environment would significantly enhance patient health. Suitable cleaning methods are those that are capable of destroying CDI spores without harming individuals (including humans and animals), such as the patients and healthcare workers within the hospital environment. Current methods for control of CDI spores utilize chemical reagents that are too harsh (such as bleach) or insufficiently sporocidal (such as alcohol) to be optimally effective.

Accordingly, there are various needs for methodologies capable of decontaminating environments containing bacterial spores, including but not limited to *Bacillus anthracis* spores and/or *Clostridium difficile* spores, preferably by degrading (e.g., neutralizing, destroying, or killing) the spores. In addition, such methodologies preferably utilize formulations whose constituents are nontoxic, human-compatible, and have high materials-compatibility, while also being conducive to safe and facile containment, delivery, and application by humans.

BRIEF DESCRIPTION OF THE INVENTION

The present invention provides methodologies, formulations, and kits suitable for decontaminating environments containing bacterial spores by degrading the spores, and in particular killing the spores, which as used herein refers to the spores being rendered incapable of germinating.

According to one aspect of the invention, formulations are provided that are suitable for killing bacterial spores each having a spore coat surrounding a spore cortex, and possibly an exosporium surrounding the spore coat. The formulations contain papain and at least one germinant.

According to another aspect of the invention, a method is provided for killing bacterial spores having a spore coat surrounding a spore cortex, and possibly an exosporium surrounding the spore coat. The method includes contacting the spores with a formulation containing papain and at least one germinant. The spore is contacted by the formulation for a duration sufficient to initiate germination of the bacterial spores. The spores are then killed with the papain in the formulation, or are rendered susceptible by the papain to being killed by a reagent.

Another aspect of the invention is to kill a bacterial spore by contacting the spore with the formulation described above to render the spore susceptible to being killed by a reagent that is a mild decontamination reagent and would be unable to kill the spore without the spore first being rendered susceptible by the formulation.

Other aspects of the invention include kits containing the formulation or components thereof described above.

Technical effects of methodologies, formulations, and kits described above preferably include the ability to use gentle, human-compatible, and materials-compatible agents in a spore decontamination or destruction method. The agents include natural degradative enzymes that, in combination with germinants, are capable of killing spores or at least rendering the spores susceptible to destruction with other agents, for example, one or more mild decontaminating chemicals. As such, the methodologies, formulations, and kits are highly conducive for use in environments in which individuals could be harmed during a treatment operation, for example, when treating surfaces of a hospital or a bacterial weaponization facility, and if used to directly treat the skin of individuals requiring decontamination.

Other aspects and advantages of this invention will be better appreciated from the following detailed description.

*cis* spores, eliminate the cortex, and severely damage the spore interior. Image A shows a plurality of treated spores. Images B and C are magnified views of individual spores of image A (identified in image A as enclosed by rectangles).

Figure 2:
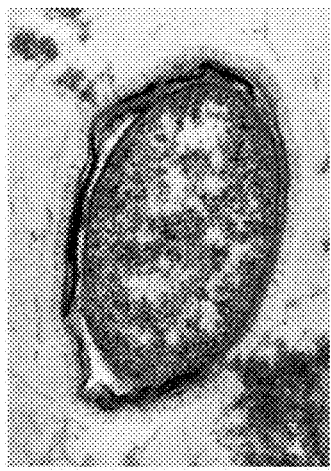
Figure 2:
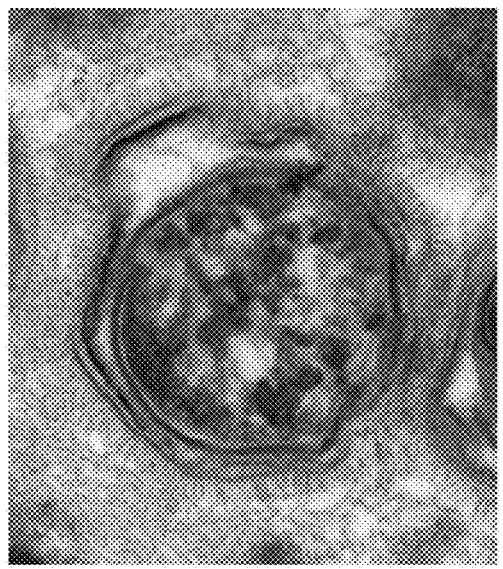
Figure 2:
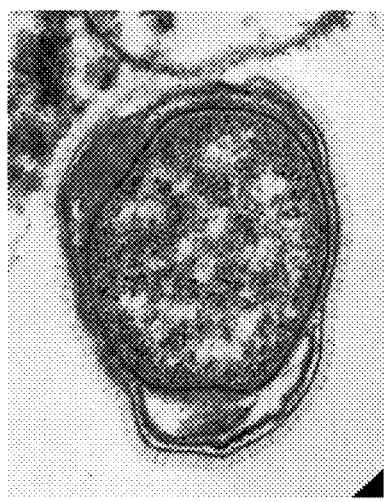

FIG. 2 includes images A, B, and C that each show individual *Bacillus anthracis* spores following treatment with a formulation containing papain as the sole enzyme and with the germinants L-alanine and inosine.

Figure 3:
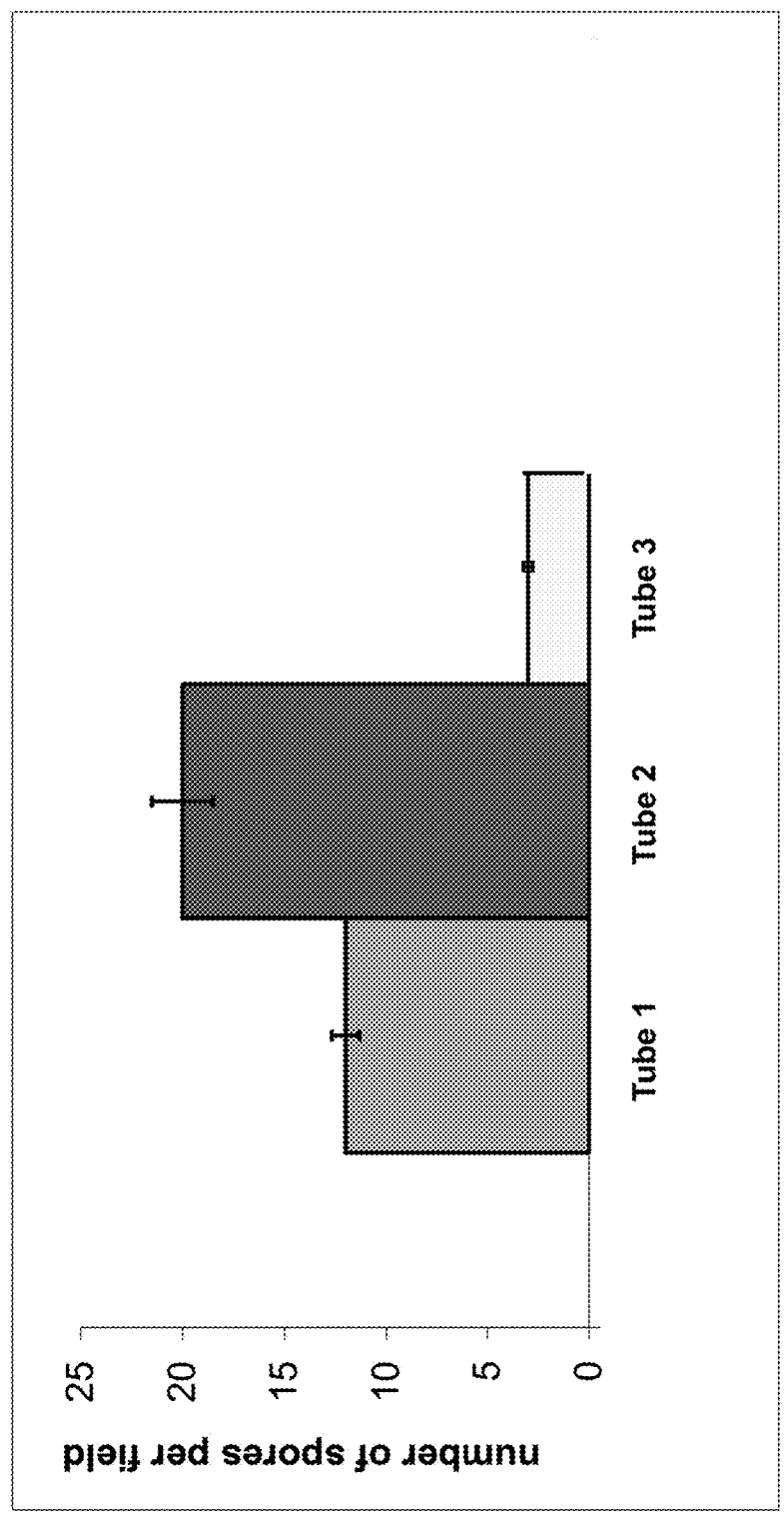
Figure 4:
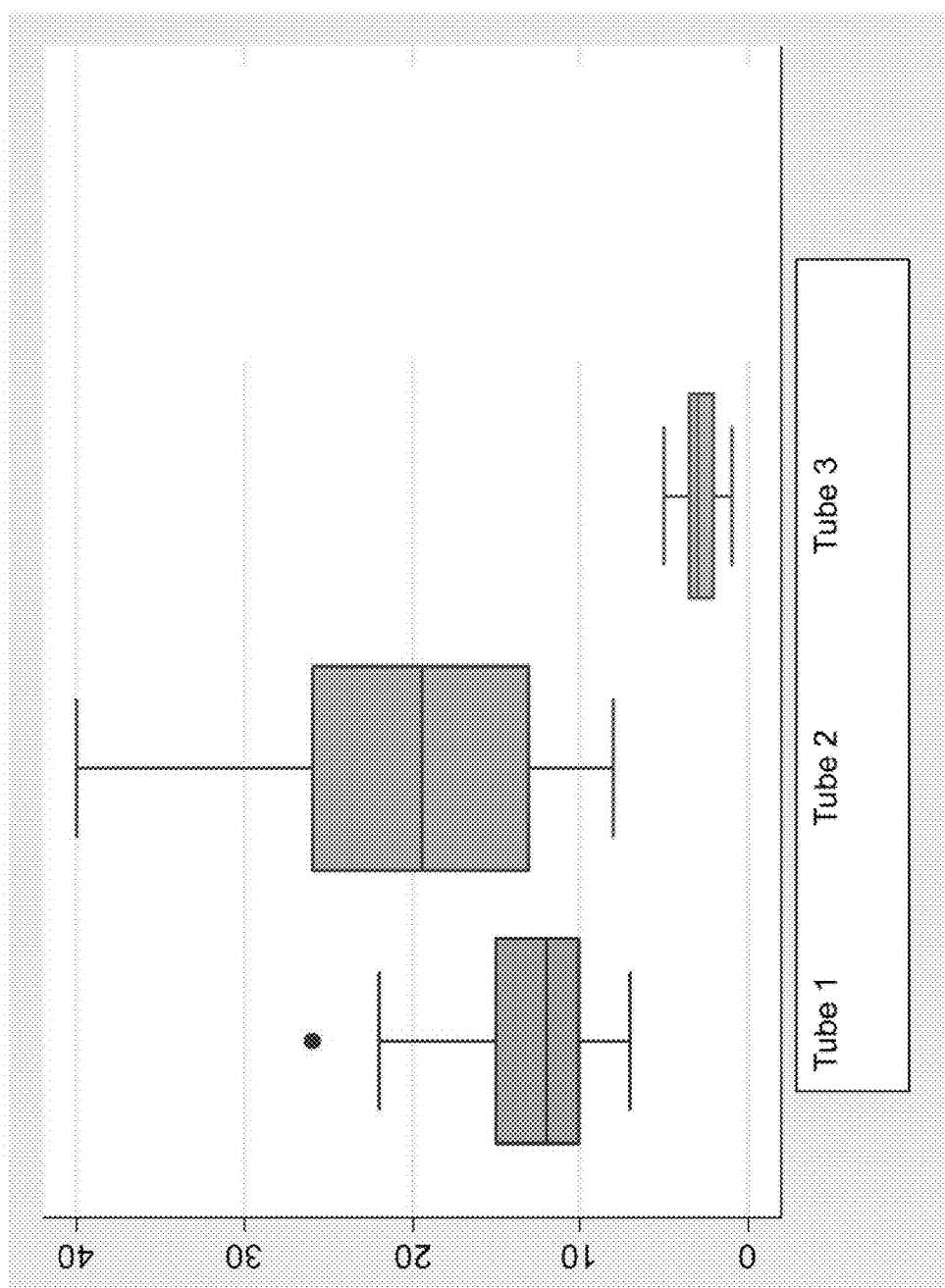

FIGS. 3 and 4 evidence the efficacy of a formulation containing papain, pancreatin and pronase in destruction of *Clostridium difficile* spores.

DETAILED DESCRIPTION OF THE INVENTION

The present invention provides methodologies, formulations, and kits for use in decontamination treatments directed at certain bacterial spores, which includes *Bacillus anthracis* spores and *Clostridium difficile* spores and may extend to spores of other bacterial species. Preferred constituents of such formulations function in combination to degrade such spores for the ultimate purpose of killing the spores, yet are nontoxic and relatively easy to contain, transport, and deliver so as to minimize any negative impact to humans and non-living materials that may be contacted by the formulations during a treatment.

Spores of particular interest to the invention can generally be described as having a spore coat surrounding a spore cortex and spore contents, and may further have an exosporium as its protective outermost layer surrounding the spore coat. Breaching the spore coat (which contains proteins, etc.) and, if present, the exosporium (which contains glycoprotein, proteins, etc.), renders the spore susceptible to attack by conventional decontamination reagents, and in some instances, as in the case of *Bacillus anthracis*, will kill the spore. A particularly notable aspect of the invention is that by breaching its spore coat, a spore can be rendered susceptible to being killed by a reagent that would otherwise be unable to kill the spore.

Formulations utilized in the methodologies are capable of degrading the spore coat and (if present) the exosporium of a bacterial spore to render its spore cortex and spore contents susceptible to attack. The formulations are enzyme-based solutions that contain, as active reagent components, at least one enzyme and at least one germinant. As used herein, the term "germinant" is understood to refer to one or more molecules specific to causing the germination of a dormant spore of a particular bacterial species, for example, *Bacillus anthracis* or *Clostridium difficile*. The formulation is introduced to a bacterial spore desired to be killed. Upon introduction of the enzyme-based formulation, the enzyme (or enzymes) and germinant (or germinants) act in combination to destroy or kill the spore. If required, the spore can be killed by continued exposure to the enzyme-based formulation and/or by the introduction of another agent, which is preferably (though not necessarily) mild and nontoxic.

The formulations may consist of the enzyme(s) and germinant(s) alone or contain the enzyme(s) and germinant (s) in combination with additional components, such as suitable carriers, stabilizers, emulsifiers, encapsulation systems, dispersal agents, and/or diluents that may be inert or active. As nonlimiting examples, the formulation may contain glycerol to facilitate dispersal, and/or the formulation may be encapsulated in a gelatin, which may act as a stabilizer.

The formulation is ultimately effective in the form of a liquid, but may initially comprise individual components that may be in the form of one or more liquids or a combination of one or more liquids and solids. The term "solids" encompasses powders that are or become dissolved in a liquid prior to use of the formulation. The formulation and its individual components can be contained and/or delivered in the form of a kit adapted to contain, deliver, and/or dispense an effective amount of the formulation in a single treatment, which can be single occurrence of short duration (entirely dispensed at one time) or continuous over a period of time, or as a series of intermittent doses. Dispensing of the formulation can entail the direct application of the formulation or combinations of its individual components onto a surface, or releasing the formulation into an existing liquid suspension of spores. In the context of treating an environment or individual, the term "kit" includes systems that allow for the storage, transport, and/or delivery of the formulation and/or any of its components in any combination. For example, a kit may include a single enclosure containing the entire formulation, or multiple enclosures containing individual components of the formulation in any combination. As used herein, the term "dose" and variants thereof in reference to the formulation and use thereof means an amount administered to an environment in need of treatment. In addition, the term "effective amount" refers to an amount of the formulation that is sufficient to at least compromise the spore such that the spore can then be killed by continued exposure to the formulation or by the introduction of one or more other agents that differ from the formulation.

Formulations particularly effective for attacking *Bacillus anthracis* and *Clostridium difficile* spores require the enzyme papain. As used herein, papain refers to any of a number of extracts, usually commercially-available and obtained from the *papaya* plant, that contain the protease papain (as well as potentially other substances). In certain embodiments of the invention, the formulation further contains pancreatin and/or pronase as additional enzymes. Pancreatin and pronase refer to any of a number of preparations of digestive enzymes, particularly (though not necessarily) protease, that are usually commercially available. Pancreatin is commonly understood to comprise the digestive enzymes amylase, lipase and protease, a notable example of the last being trypsin. Pronase is commonly known as a proteolytic enzyme obtained from *Streptomyces griseus* and containing mixtures of proteases. Papain, pancreatin, and pronase are typically available in liquid and/or powder form. When these enzymes are used together in a formulation, the liquid or powder forms are combined in water or a conventional enzyme buffer (such as a tris buffer), enabling the formulation to be applied to spores in liquid form. Individual spores can be sufficiently compromised by the enzyme-based formulation to cause death to the spores, or death can occur as a result of subsequent exposure to one or more decontamination reagents, preferred examples of which are relatively mild decontamination reagents such as ethanol or a mild detergent.

Notably, papain, pancreatin, and pronase are nontoxic to humans, as are the germinants of interest to the present invention. As such, containment, delivery, and dispensing of the individual reagents and a formulation containing any combination of these reagents are relatively facile and simple, and can be accomplished in a wide range of environments and situations.

Because the reagents discussed above are nontoxic, human-compatible, and materials-compatible, the formulations containing the reagents can be useful in environments such as hospitals where numerous individuals, including patients, doctors, and staff, may inadvertently come into contact with the formulation, or in harsh environments in which containment, transport, and application of the formulation can be challenging to the individuals performing decontamination with the formulation.

Figure 1:
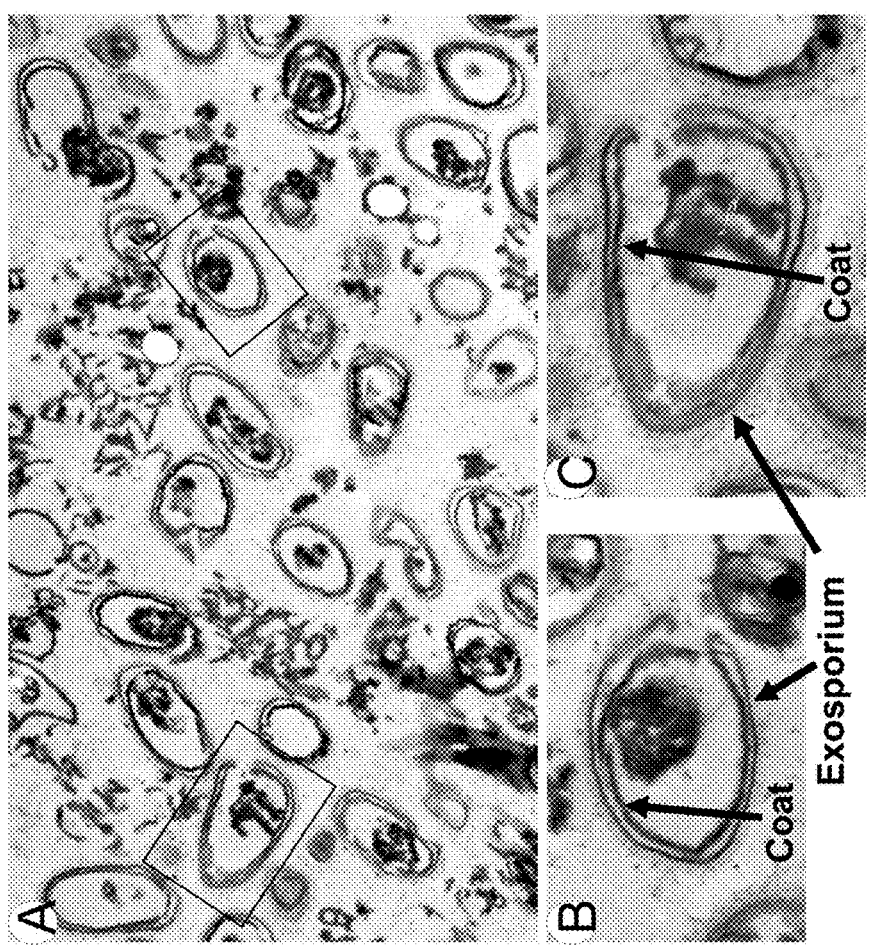
FIG. 1 includes images A, B, and C and shows the ability of a formulation containing papain, pancreatin, and pronase to breach the exosporium and spore coat of *Bacillus anthra-*

In one investigation leading to the present invention, formulations containing papain, pancreatin and pronase as reagents were shown to be effective treatments for *Bacillus anthracis* spores. In particular, enzyme-based formulations containing papain, pancreatin and pronase were effective in killing *Bacillus anthracis* spores without necessitating any subsequent treatments. In this investigation, three one-hour applications of the three-enzyme formulation are applied successively. Thin-section electron microscopy demonstrated that the formulation breached the exosporium and spore coat, eliminated the cortex, and severely damaged the spore interior (FIG. 1). Further analysis and observations relating to this investigation led to the conclusion that a low level of one or more germinants was present in the formulation, possibly L-alanine in the pancreatin, and that the ability of the formulation to damage and, thereby, kill spores depended, at least in part, on the presence of one or more germinants in the formulation, indicating that a component of efficient enzyme-based spore killing is the ability to induce germination. Overall, the investigation indicated that, for the investigated three-enzyme formulation to cause significant damage to any spore structure, at least some germination must take place. Based on analysis of spore viability using counting of colony forming units, a kill rate of over 3 $\log_{10}$ was routinely achieved with formulations containing papain, pancreatin and pronase as reagents and the low levels of germinants already present in one or more of the enzyme preparations.

Subsequent investigations combined papain (without any other enzymes) with germinants appropriate for *Bacillus anthracis* (specifically, L-alanine and inosine). FIG. 2 shows *Bacillus anthracis* spores treated by this formulation. In these spores, the exosporium seen in FIG. 2 appears contiguous (though not completely intact, as discussed below), the coat is partially disassembled, and the cortex is not present. The spore interior is swollen and appears punctate, consistent with the rehydration that is typical during germination. Based on analysis of spore viability using counting of colony forming units, a kill rate of over 5 $\log_{10}$ was routinely produced with formulations containing papain as the sole enzyme and L-alanine and inosine as germinants. As a result, it was inferred that most if not all the spores in FIG. 2 were killed. In these spores, it was also inferred that the exosporium had become porous to papain and, most likely, the papain has reached the spore interior and, by doing so, has killed the spore. Overall, the data indicated that, as in the prior formulation containing combinations of papain, pancreatin and pronase as enzyme reagents, at least some germination is essential for significant spore damage.

In another investigation, *Clostridium difficile* spores were treated with a formulation containing papain, pancreatin and pronase as reagents. A six day-old biofilm culture of *Clostridium difficile* strain B117 was used. Cells grown on four filters were pooled together and washed three times with sterile water. Cells were then divided into three tubes and spun down. Each tube was treated according to a separate experimental protocol: Tube 1 (negative control): Incubated at about 65° C. for about one-half hour in a water bath to kill vegetative cells, and then left at room temperature for about three hours. Tube 2 (negative control): Incubated at about 40° C. for about three hours in a buffer used for enzyme preparation. Tube 3: 1 ml of the formulation was added. Thereafter, incubated for about three hours at about 40° C., replacing the formulation every hour.

Each tube was then washed with water two times to remove reagents and resuspended in about 50 µl of water to concentrate the spores, which were then counted by light microscopy. FIG. 3 is a graph showing the data in a "classic" manner that emphasizes the standard errors of the mean. FIG. 4 is a graph showing the distribution of the spore count data. Two slides per sample were counted, for a total of about thirty to thirty-five fields. FIGS. 3 and 4 clearly evidence the efficacy of the formulation in destruction of *Clostridium difficile* spores.

In view of the above, the investigations demonstrated that formulations described herein were effective for destruction of *Clostridium difficile* and *Bacillus anthracis* spores. Although an understanding of the mechanism by which the formulations provides this effect is not necessary to practice the present invention and the present invention is not limited to any particular mechanism of action, the presence of one or more germinants in the formulations was concluded to have allowed the enzymes (either papain alone or in combination with the additional enzymes pancreatin and pronase) to penetrate and/or degrade or destroy the exosporium and to degrade or destroy the spore coats of the spores, after which the spores were killed as a result of continued treatment with the formulation. However, as a result of the spore coat and exosporium being compromised by the formulation, it was concluded that the spores had been rendered sufficiently susceptible by the formulation to allow the spores to be killed by further treatment with a different reagent, preferably a relatively gentle reagent, nonlimiting examples of which include ethanol or a mild detergent.

Based on the experiments described above, it is believed that an effective formulation for the destruction of bacterial spores, for example, such as *Bacillus anthracis* spores and *Clostridium difficile* spores, introduces at least 10 mg/ml of papain, and for *Bacillus anthracis* at least 100 mM of L-alanine and/or at least 50 mM of inosine, and optionally at least 10 mg/ml of another enzyme such as pancreatin and/or pronase to a solution containing up to about $10^7$ spores per milliliter. A dose of the formulation to a volume of bacterial spores, in the context of the present invention, should be sufficient to at least reduce viability by $10^5$ logs over a reasonable time frame. One skilled in the art will recognize that dosage will depend upon a variety of factors, including the condition of the spores, amount of spores, concentration and types of reagents in the formulation, number of treatments, etc. The size of the dose also will be determined by the route, timing and frequency of administration as well as the existence, nature, and extent of any adverse side effects that might accompany the administration of the formulation and the desired destructive effect. Appropriate dosing may be determined empirically from experimental trials.

While the invention has been described in terms of specific embodiments, it is apparent that other forms could be adopted by one skilled in the art. For example, the enzyme-based formulations could be modified appropriately to act on bacterial spores of species other than those discussed herein, and various containment and/or delivery parameters could be used. Therefore, the scope of the invention is to be limited only by the following claims.

The invention claimed is:

1. A method of killing bacterial spores present in a facility, the bacterial spores each having a spore coat surrounding a spore cortex and optionally an exosporium surrounding the spore coat, the method comprising:

preparing a formulation by combining papain and at least one germinant in an amount sufficient to initiate germination of the bacterial spores present in the facility;

contacting the bacterial spores with the formulation by dispensing the formulation within the facility, the bacterial spores being contacted by the formulation for a duration sufficient to initiate germination of the bacterial spores with the at least one germinant; and further dispensing a decontamination reagent to the bacterial spores, wherein the reagent would be unable to kill the bacterial spores without breaching the spore coats of the bacterial spores; and wherein the bacterial spores in which at least some germination has taken place are killed by the papain in the formulation and/or by the reagent.

2. The method according to claim 1, wherein the bacterial spores are killed by the papain in the formulation.

3. The method according to claim 1, wherein the bacterial spores are killed by the reagent.

4. The method according to claim 3, wherein the reagent is chosen from the group consisting of ethanol and detergents.

5. The method according to claim 1, wherein the at least one germinant comprises at least L-alanine.

6. The method according to claim 1, wherein the at least one germinant comprises at least inosine.

7. The method according to claim 1, wherein the bacterial spores are *Bacillus anthracis* spores.

8. The method according to claim 1, wherein the bacterial spores are *Clostridium difficile* spores.

9. The method according to claim 1, wherein the formulation contains at least 10 milligrams of the papain in the formulation.

10. The method according to claim 1, wherein the formulation contains at least 50 mM of the at least one germinant.

11. The method according to claim 1, wherein the formulation further contains one or more additional enzymes.

12. The method according to claim 11, wherein the one or more additional enzymes comprise pancreatin and pronase.

13. The method according to claim 1, wherein the facility is a hospital and the formulation is applied to surfaces within the hospital.

14. The method according to claim 1, wherein the facility produces the bacterial spores and the formulation is dispersed within the environment of the facility.

15. A method of killing bacterial spores present in a facility, the bacterial spores each having a spore coat surrounding a spore cortex and optionally an exosporium surrounding the spore coat, the method comprising:

preparing a formulation by combining papain with L-alanine and inosine as germinants in an amount sufficient to initiate germination of the bacterial spores present in the facility;

contacting the bacterial spores with the formulation by dispensing the formulation within the facility, the bacterial spores being contacted by the formulation for a duration sufficient to initiate germination of the bacterial spores with the germinants; and further dispensing a decontamination reagent to the bacterial spores, wherein the reagent would be unable to kill the bacterial spores without breaching the spore coats of the bacterial spores; and wherein the bacterial spores in which at least some germination has taken place are killed by the papain in the formulation and/or by the reagent.

16. The method according to claim 15, wherein the bacterial spores are *Bacillus anthracis* spores or *Clostridium difficile* spores.

17. A method of killing bacterial spores present in a facility, the bacterial spores each having a spore coat surrounding a spore cortex and optionally an exosporium surrounding the spore coat, the method comprising:

preparing a formulation by combining papain, pancreatin, pronase, and at least one germinant in an amount sufficient to initiate germination of the bacterial spores present in the facility;

contacting the bacterial spores with the formulation by dispensing the formulation within the facility, the bacterial spores being contacted by the formulation for a duration sufficient to initiate germination of the bacterial spores with the at least one germinant; and wherein the bacterial spores in which at least some germination has taken place are killed by the papain in the formulation.

* * * * *